United States Patent
Robbins et al.

(10) Patent No.: US 6,203,999 B1
(45) Date of Patent: *Mar. 20, 2001

(54) DETECTION OF PROSTATE AND OTHER CANCERS BY ASSAYING FOR CANCER-SPECIFIC ANTIGENS HAVING LINKED OLIGOSACCHARIDES WHICH ARE AT LEAST TRIANTENNARY

(75) Inventors: Phillips W. Robbins, Acton; Sadhana Prakash, Cambridge, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/231,004

(22) Filed: Jan. 14, 1999

Related U.S. Application Data

(62) Division of application No. 08/887,468, filed on Jul. 2, 1997, now Pat. No. 5,902,725.
(60) Provisional application No. 60/021,109, filed on Jul. 3, 1996.

(51) Int. Cl.[7] .................................................. G01N 33/567
(52) U.S. Cl. ......................................... 435/7.21; 435/7.23
(58) Field of Search .................................... 435/7.1, 7.21, 435/7.23; 436/63, 64

(56) References Cited

U.S. PATENT DOCUMENTS

| 5,427,914 | 6/1995 | Dennis | 435/7.23 |
| 5,902,725 | * 5/1999 | Robbins et al. | 435/7.1 |

FOREIGN PATENT DOCUMENTS

| WO 95/18381 | 7/1995 | (WO) . |

OTHER PUBLICATIONS

Oellerich, *J. Clin. Chem. Clin. Biochem.*, vol. 22, pp. 895–904 (1984).
Yamashita, et al., *J. Biol. Chem.*, vol. 259, No. 17, pp. 10834–10840 (Sep. 10, 1984).
Hubbard, *J. Biol. Chem.*, vol. 262, No. 34, pp. 16403–16411 (Dec. 5, 1987).
Hakomori, *Advances in Cancer Research*, VandeWoude, et al., eds., vol. 52, pp. 257–331, Academic Press, Inc., New York (1989).
Hudson, et al., *J. Urology*, vol. 142, pp. 1011–1017 (Oct. 1989).
Young, et al., *Cancer Research*, vol. 51, pp. 3748–3752 (Jul. 15, 1991).
Oesterling, *J. Cell. Biochem.*, Supp. 16H, p. 31 (1992).
Muramatsu, *Glycobiology*, vol. 3, No. 4, pp. 294–296 (1993).
Villoutreix, et al., *Protein Sci.*, vol. 3, p. 2033 (1994).
Zhang, et al., *Clin. Chem.*, vol. 41, p. 1567 (1995).
Belanger, et al., *The Prostate*, vol. 27, pp. 187–197 (1995).
Banerjee, et al., *Human Pathology*, vol. 26, No. 9, pp. 1005–1013 (Sep. 1995).

* cited by examiner

*Primary Examiner*—Sheela Huff
(74) *Attorney, Agent, or Firm*—Elliot M. Olstein; Raymond J. Lillie

(57) ABSTRACT

A process for assaying for cancer of the prostate, comprising assaying a sample derived from a human for prostate specific antigen having a linked oligosaccharide which is at least triantennary. The assay may employ a binding molecule which binds to oligosaccharides that are at least triantennary, but does not bind to oligosaccharides that are monoantennary or diantennary. Such binding molecule may be a lectin such as PHA-L or an antibody to an oligosaccharide that is at least triantennary.

2 Claims, 1 Drawing Sheet

DETECTION OF PROSTATE AND OTHER CANCERS BY ASSAYING FOR CANCER-SPECIFIC ANTIGENS HAVING LINKED OLIGOSACCHARIDES WHICH ARE AT LEAST TRIANTENNARY

This is a divisional of application Ser. No. 08/887,468 filed Jul. 2, 1997, now U.S. Pat. No. 5,902,725, which claims priority under 35 U.S.C. 119(e) based on provisional application Serial No. 60/021,109, filed Jul. 3, 1996.

FIELD OF THE INVENTION

The present invention relates to the field of cancer immunoassays. Specifically, provided is an immunoassay method for detection of the prostatic-specific antigen (PSA). The immunoassay of the present invention distinguishes between normal prostatic-specific antigen and abnormal prostatic-specific antigen, i.e., PSA that is related to the presence of a carcinoma of the prostate.

BACKGROUND OF THE INVENTION

Despite the widely accepted use of PSA as a marker for prostate cancer, this molecule has not yet been completely characterized. Past studies have established, however, using both amino acid and cDNA sequencing techniques, that PSA contains 237 amino acids, with a molecular mass of 26,079 Da for the peptide moiety of the molecule. The predominant PSA molecular species detected by ion spray mass spectrometry (ISMS) was at relative molecular mass of 28,430, indicating that PSA contains a carbohydrate residue having a molecular weight of 2,351 for a total weight percentage of carbohydrate of 8.3% (Belanger, A., et al., *Prostate*, 27:187–197 (1995)). PSA is a kallikrein-like serine protease that is produced exclusively by the epithelial cells of all types of prostatic tissue, benign and malignant. Physiologically, it is present in the seminal fluid at high concentration and functions to cleave the high-molecular weight protein responsible for the seminal coagulum into smaller polypeptides. (Oesterling, J. E., *J. Cell Biochem. Suppl.*, 16H:31–43 (1992))

Prostate-specific antigen was first described by Wang, M.C., et al., *Invest. Urol.*, 17:159 (1979). It is a secretion of prostate epithelium and is also produced by prostate cancer cells. PSA was characterized as a glycoprotein monomer with protease activity. More recently, the amino acid sequence of the antigen has been reported (Watt, W. K., et al., *PNAS USA*, 83:3166 (1986)) and the gene for PSA has been cloned (Lundwall, A., *Biochem. Biophys. Res. Commun.*, 161:1151 (1989)).

A variety of carbohydrate markers have been used to reveal the importance of carbohydrate information in the clinical characteristics of human carcinomas. Consequently, carbohydrate profiles of the primary tumor have been correlated with tumor grade, metastatic potential and prognosis, which are not mutually unrelated. Oncogenesis is usually associated with alterations in cell surface carbohydrate structure, and tumor-associated carbohydrate markers have been utilized in the diagnosis and followup of human cancers. (Hakomori, S. , *Adv. Cancer Res.*, 52:257–331 (1989).) Recently, it has been shown that carbohydrate structures on the tumor cell surface are associated with the metastatic potential of tumor cells.

The association of carbohydrate signals with metastatic potential was first revealed in experimental systems. Notably, β1→6 branching of asparagine-linked oligosaccharides, which are increased in a number of tumor cells (Yamashita, K., et al., *J. Biol. Chem.*, 259:10834–10840 (1984), and in metastases of murine melanomas and fibrosarcomas (Dennis, J. W., et al., *Science*, 236:582–585 (1987)). N-linked glycosylation is initiated in mammalian cells, as in those of all higher eukaryotes, with the transfer of the precursor oligosaccharide to accepted asparagine residues of nascent or newly synthesized proteins. Subsequent modification of this oligosaccharide generates the extreme diversity of N-linked oligosaccharides found in mature glycoproteins. Steric accessibility to Golgi enzymes appears to determine whether the processing of a given N-linked glycan stops at the oligomannose stage or proceeds further (Hsieh, P., et al., *J. Biol. Chem.*, 258:2555–2561 (1983)). However, the regulation of the later stages of processing, in which a wide variety of bi, tri, and tetraantennary complex glycans are synthesized, is only poorly understood. This regulation is of special interest because it is altered in many differentiating (Feizi, T., *Nature*, 314:53–57 (1985)) or oncogenically transformed (Warren, L., et al., *Biochem. Biophys. Acta.*, 516:97–127 (1978)) cells, resulting in a shift in an N-linked oligosaccharide composition. This is likely to have physiologically significant consequences, since altered protein glycosylation can affect processes such as adhesion, metastasis and immune recognition. (Hubbard, S. C., *Journal of Biological Chemistry*, 262 (34):16403–16411 (1987).)

The proposed carbohydrate structure of PSA is a diantennary N-linked oligosaccharide of the N-acetyllactosamine type, with a sialic acid group at the end of each of the two branches. Approximately 70% of the PSA molecules contain a fucose group in the core chitobiose moiety. PSA contains only one N-linked chain, which is linked to asparagine[45] (Watt, et al., *Proc. Nat. Acad. Sci.*, Vol. 83, pgs. 3166–3170 (1986); Schaller, et al., *Eur. J. Biochem.*, Vol. 170, pgs. 111–120 (1987); Riegman, et al., *Biochem. Biophys. Res. Commun.*, Vol. 155, pgs. 181–188 (1988); Van Halbeek, *Methods in Molecular Biology*, Jones, et al., eds., Totowa, N. J., Humana Press, pgs. 115–148 (1993); Lundwall, et al., *FEBS Lett.*, Vol. 214, pgs. 317–322 (1987)). Van Halbeek, et al. suggest that this protein is composed of several isoforms whose structure may differ in their carbohydrate composition.

The proposed carbohydrate structure of PSA confirms that only one glycosylation site in the protein is occupied. This glycosylation site is readily identified based on the amino acid sequence of the protein; the only consensus ASN-X-SER/THR sequence in PSA is found at residue 45-46-47 (ASN-LYS-SER). (Belanger, et al.). The complete characterization in the structure of the carbohydrate side-chain of PSA has been determined by Belanger, et al.

Carcinoma of the prostate has long been regarded as an unpredictable disorder which makes sound therapeutic decisions in evaluating the results of different types of treatment very difficult. Prostate cancer is unique among the potentially lethal human malignancies in that there is a wide discrepancy between the high prevalence of histologic changes recognizable as cancer and the much lower prevalence of clinical disease.

The concept that adenocarcinoma of the prostate exists in a latent and a clinical form is supported by epidemiologic, pathologic and clinical evidence. Although these divergent manifestations of prostate cancer have come in architectural and cytologic features, they can be distinguished from each other to some degree by differences in certain pathologic features, such as the volume, grade, and invasiveness of the lesion.

Prostate cancer has become the most common cancer among American men, and only lung cancer is responsible for more cancer deaths (Boring, C. C., Cancer Statistics, 41:19–36 (1991)) The age specific mortality rate has slowly increased over the past 50 years and in black American men is nearly double the rate found in white men (Carter, H. B., Prostate, 16:39–48 (1990)). Prostate cancer is responsible for nearly three percent of all deaths in men over the age of 55 years (Seidman, H., et al., Probabilities of Eventually Developing or Dying of Cancer-United States, 35:36–56 (1985)). Since the incidence of prostate cancer increases more rapidly with age than any other cancer, and the average age of American men is rising, the number of patients with prostate cancer is expected to increase dramatically over the next decade.

Approximately 30% of men with prostate cancer have distant metastases at the time of diagnosis (Schmidt, J. D., et al., J. Urol., 136:416–421 (1986)). Despite the impressive symptomatic response of metastases to hormonal manipulation (androgen deprivation), the survival rate for these patients is dismal: the median duration of survival is less than three years (Eyar, D. P., Urologic Pathology: The Prostate, Philadelphia, Pa., Lea and Febiger, 241–267 (1977)). By five years, over 75% and by ten years, more than 90% of these patients die of their cancer rather than with it (Silverberg, E., Cancer, 60:692–717 (1987) (Suppl.)).

The problem with prostate cancer is that many forms of prostate cancer are latent, in other words, such forms are difficult to detect. Approximately 30% of the men over the age of 50 years who have no clinical evidence of prostate cancer harbor foci of cancer within the prostate (McNeal, J. E., et al., The Lancet, January, 11:60–63 (1986)). This remarkably high prevalence of prostate cancer at autopsy, seen in no other organ, makes it the most common malignancy in human beings (Dhom, G., J. Cancer Res. Clin. Oncol., 106:210–218 (1983)). There is strong support for the concept of multi-step process in the pathogenesis of prostate cancer in which latent cancers progress through some but not all of the steps necessary for full malignant expression (Utter, H. B., et al., J. Urol., 143:742–746 (1990).

There are a variety of techniques for early detection and characteristics of prostate cancers, however, none of them are devoid of any problems. Prostate cancer is a notoriously silent disease with few early symptoms. Symptoms associated with bladder outlet obstruction are commonly present in men over the age of 50 years and are often ascribed to benign prostatic hyperplasia (BPH).

Digital rectal examination (DRE) traditionally has been considered the most accurate test for the detection of prostate cancer. DRE has been demonstrated to be more sensitive, more specific, and to have a greater efficiency than a variety of laboratory tests available, however, few of these laboratory tests are still in clinical use today (Guinan, P., et al., N. Engl. J. Med., 303:499–503 (1980)). DRE detects cancer relatively late, and there is only a weak correlation between the size of the cancer estimated by DRE and the actual volume of cancer present. The most serious limitation of DRE is its lack of sensitivity (false negative results). For example, approximately 10% to 20% of transurethral resections performed for benign prostatic hypertrophy in patients with no palpable abnormalities suggestive of cancer uncover an incidental cancer of the prostate. DRE detected only 12 of 22 cancers found in a screening study, while transrectal ultrasonography (TRUS) found 20 (Lee, F., et al., Radiology, 168:389–394 (1988)). Thus, DRE is relatively insensitive and nonspecific. Cancers detected by palpation are relatively large, late in their development and no longer curable, and some are very small, such that they are clinically unimportant cancers.

Patients having prostate cancer have an elevated prostate-specific antigen level. Cancer was detected in 26% of the men with a PSA level of 4.0 to 10.0 ng/ml. Serum PSA levels have been shown to correlate generally with the volume, clinical stage, and pathologic stage of prostate cancer, although there is a wide range of PSA values associated with any given volume or stage (Hudson, M. A., J. Urol., 142:1011–1017 (1989)). PSA, however, is not predictive of the features of the cancer in the individual patient. If the level of PSA is greater than 10.0 ng/ml, 57% to 92% of the patients will have locally advanced cancer. Therefore, while more specific, using a PSA level higher than 10 ng/ml may not offer an effective technique for early detection. There are other theoretical limitations to the use of this serum marker for early detection. A normal serum PSA level does not exclude the diagnosis of cancer. False-negative results are common, and a third of men treated with radioprostatectomy for prostate cancer have a normal serum PSA level. False-positive results are also common since PSA levels are often elevated in men with common benign conditions, such as BPH or prostatitis. In summary, PSA levels have proved to be extremely useful in the early detection of prostate cancer, especially when combined with DRE or TRUS. A PSA level detection, however, must be used in combination with DRE or TRUS in order to be sure that what is present is cancer and not BPH or prostatitis.

The introduction of TRUS has provided physicians with an effective way to see the internal anatomy and pathology of the prostate gland. TRUS has been used to screen for prostate cancer in several large series and has consistently been shown to increase detection when compared with DRE. TRUS is performed by taking a sonograph of the pelvic area and perhaps the most important use of TRUS in the early detection of prostate cancer is as a guide for directed needle biopsies of the prostate (Lee, F., et al., Radiology, 170:609–615 (1989)).

PSA testing can have significant value in detecting metastatic or persistent disease in patients following surgical or medical treatment of prostate cancer (Lange, P. H., et al., Urology, 33 (6 Suppl.):13 (1989); and Killian, C. F., et al., Cancer Res., 45:886 (1985)). Persistent elevation of PSA following treatment or an increase in the post-treatment base-line PSA level is indicative of recurrent or residual disease (Brawer, M. K., et al., Urology, 33 (5 Suppl.):11 (1989)). Although PSA is prostate-specific, it is not prostate-cancer specific. As a result, benign conditions such as benign prostatic hyperplasia, prostatitis and infarction, as well as prostatic intraepithelial neoplasia, can be associated with elevated serum levels of PSA. (Osterling, J. E., J. Cell. Biochem. Suppl., 16H:31–43 (1992).)

Measurement of serum levels of PSA is widely used for diagnosis of prostate cancer and benign hypoplasia of prostate tissue. This serum marker is of value since it is derived only from the tissue of interest, but increased levels of PSA in serum do not allow a completely clear-cut diagnosis of benign versus malignant changes.

Accordingly, there is a need in the art to obtain an accurate diagnosis of prostate cancer through non-invasive techniques. There is also a clear need for diagnosing prostate cancer via detection of an altered form of PSA derived from a biological sample of the patient.

In accordance with an aspect of the present invention, there is provided a process for assaying for cancer associated with the presence of antigens having linked oligosaccharides which are at least triantennary, such as, for example, cancer of the prostate. The process comprises assaying a sample derived from a human for an antigen, such as, for example, prostatic-specific antigen or prostate specific antigen, having linked oligosaccharides which are at least triantennary.

The terms "prostatic-specific antigen" or "prostate specific antigen" (PSA), as used herein, mean a 237-residue protease with a molecular mass of approximately 26,079 daltons, or a derivative or analogue thereof, which is expressed nearly exclusively by human prostatic epithelial cells.

The term "antennary", as used herein, means the number of linkages of an N-linked oligosaccharide attached to an amino acid residue, such as, for example, $Asp^{45}$, of PSA. The term "antennary" is preceded by the prefixes bi-, tri-, and tetra-, etc. These prefixes refer to the number of branches of the oligosaccharide.

Prostate cancers which may be detected in accordance with the present invention include metastatic prostate cancers and non-metastatic prostate cancers.

Although the scope of the present invention is not to be limited to any particular theoretical reasoning, Applicants have found unexpectedly that, unlike normal PSA, which bears only biantennary oligosaccharide, PSA from prostate cancer has a mixture of biantennary and triantennary oligosaccharides. Such triantennary oligosaccharides, which are linked to an amino acid residue of PSA such as Asp 45, are associated with oncogenic transformation.

To determine the presence of the oligosaccharides which are at least triantennary, and which are N-linked to an amino acid residue, such as asparagine 45 of PSA, in one embodiment, prostatic-specific antigen is isolated from a biological sample derived from a patient. The biological sample includes, but is not limited to, serum, plasma, prostatic fluid, semen, urine, and spinal fluid. Subsequent to the isolation of PSA from the biological sample, the presence of N-linked oligosaccharides which are at least triantennary is determined.

Isolation of PSA may be performed by numerous methods which are well-known to those of the skill in the art. See Sambrook, et al., *Molecular Cloning; A Laboratory Manual*, 2nd ed., Cold Spring Harbor, N.Y., 1989, the disclosure of which is hereby incorporated by reference in its entirety.

For example, the PSA may be isolated and purified by methods including ammonium sulfate or ethanol precipitation, acid extraction, anion or cation exchange chromatography, phosphocellulose chromatography, hydrophobic interaction chromatography, affinity chromatography, and hydroxyapatite chromatography. Protein refolding steps can be used, as necessary, in completing configuration of the protein. Finally, high performance liquid chromatography can be employed for final purification steps.

In a preferred embodiment of the present invention, PSA is isolated through the use of an antibody, preferably bound to a solid support, which recognizes an epitope of PSA. The antibody may be polyclonal or monoclonal, preferably monoclonal.

The bound PSA then is contacted with a compound or binding molecule which binds to oligosaccharides which are at least triantennary. Such compound does not bind to oligosaccharides that are monoantennary or diantennary. Examples of compounds or binding molecules which bind to oligosaccharides which are at least triantennary, but do not bind to oligosaccharides which are monoantennary or diantennary, include, but are not limited to, the lectin PHA-L from red kidney bean (Phaseolus vulgaris), and antibodies which specifically bind to oligosaccharides which are at least triantennary. Such antibodies may be prepared by procedures known in the art. Such lectin also is available from Sigma labeled with biotin or cross-linked to beaded agarose. PHA-L also is described in Fu, et al., *Anal. Biochem.*, Vol. 1, pgs. 53–63 (October 1992).

The binding molecule which binds to an oligosaccharide which is at least triantennary may be conjugated to a detectable marker or label. Examples of such detectable markers or labels include, but are not limited to, fluorescent labels, radioisotopes, such as, for example, isotopes of iodine, cobalt, or tritium, spin labels, chemiluminescent materials, enzymes, absorbing dyes, biotin, or colored particles.

After the bound PSA is contacted with the labeled binding molecule, the free (unbound) binding molecule is separated from the binding molecule which has been bound. The presence of prostate specific antigen having linked oligosaccharides which are at least triantennary then is determined by detecting the label of the binding molecule that is bound to oligosaccharides which are at least triantennary, said oligosaccharides being linked to prostate specific antigen. Such presence may be determined by means known to those skilled in the art, such means being dependent upon the type of label employed. The presence of a label indicates that the bound PSA includes linked oligosaccharide which is at least triantennary, with the presence of such structure being indicative of prostate cancer.

In accordance with another aspect of the present invention, there is provided a kit or package for detecting prostate specific antigen linked to an oligosaccharide which is at least triantennary. The kit includes (a) a solid support upon which is supported a binder, in particular, an antibody, which recognizes an epitope of prostate specific antigen; and (b) a binding molecule having a label such as those hereinabove described, wherein the binding molecule binds oligosaccharides that are at least triantennary but are not monoantennary or diantennary.

Solid supports which may be employed include, but are not limited to, those made of cellulosic materials such as paper, cellulose, and cellulose derivatives such as cellulose acetate and nitrocellulose; silica; fiberglass; inorganic materials such as deactivated aluminum, diatomaceous earth, or other inorganic finely divided material dispersed uniformly in a porous polymer matrix made of polymers such as vinyl chloride-propylene copolymer and vinyl chloride-vinyl acetate copolymer; cotton; nylon; porous gels such as silica gel, agarose, dextran, and gelatin; polymeric films such as polyacrylamide; magnetic particles; microtiter plates; polystyrene tubes; protein-binding membranes; Sephadex (Pharmacia Fine Chemicals, Inc., Piscataway, N.J.); Trisacryl (Pointet-Girard); silicon particles; polystyrene particles; vinyl chloride particles; latex particles; and porous fibrous matrices. In one embodiment, the solid support includes synthetic microparticles of polystyrene, vinyl chloride, or latex, having a diameter of 0.1 to 10 microns.

In another alternative, two assays are conducted. The first assay involves an inhibition assay. In such an assay, a compound or binding molecule, such as those hereinabove described, which binds to oligosaccharides which are at least triantennary, but does not bind oligosaccharides which are monoantennary or diantennary, is incubated with a predetermined amount of a first portion of a sample suspected of containing prostate specific antigen. After such incubation, the sample is contacted with an antibody supported on a solid support. The supported antibody, which may be a monoclonal or polyclonal antibody, recognizes an epitope of prostate specific antigen which, if an an oligosaccharide which is at least triantennary is present on the prostate specific antigen, is proximal to such oligosaccharide of prostate specific antigen which is at least triantennary, whereby binding of the PSA antigen to the supported antibody is inhibited by the compound which binds to the oligosaccharide which is at least triantennary. If prostate specific antigen having linked oligosaccharides which are at least triantennary is present in such sample, such prostate specific antigen will not be able to bind to the supported antibody due to the previous binding of the compound or binding molecule which binds oligosaccharides which are at least triantennary. If there is prostate specific antigen present in the sample which does not include oligosaccharides which are at least triantennary, such prostate specific antigens will bind to the solid support. Thus, any prostate specific antigen which binds to the supported antibody is prostate specific antigen which does not have linked oligosaccharides which are at least triantennary.

Bound PSA then is separated from free PSA. The sample then is contacted with a labeled antibody which recognizes an epitope of prostate specific antigen. Thus, the labeled antibody binds to prostate specific antigen which has been bound by the supported antibody. Bound labeled antibody then is separated from free labeled antibody. The amount of bound labeled antibody to prostate specific antigen then is determined.

In the second assay, which is a sandwich assay, the antibody to prostate specific antigen which is supported on a solid support is contacted with a second portion of the sample suspected of containing prostate specific antigen. The second portion contains an amount of sample identical to that of the first portion. After the sample has contacted the solid support, the labeled antibody to prostate specific antigen is added, and the amount of bound labeled antibody is determined. If the amounts of bound labeled antibody in the first assay and the second assay are the same, then no prostate specific antigen linked to an oligosaccharide which is at least triantennary is present in the sample. If the amount of bound labeled antibody in the second assay is greater than that in the first assay, then prostate specific antigen which is linked to an oligosaccharide which is triantennary is present in the sample.

Thus, in accordance with a further aspect of the present invention, there is provided a kit or package for detecting prostate specific antigen linked to an oligosaccharide which is at least triantennary. The kit includes a pair of solid supports. Each support includes a binder, in particular, an antibody, which recognizes an epitope of prostate specific antigen. The epitope is located proximal to an oligosaccharide which is at least triantennary, if such an oligosaccharide is present on the prostate specific antigen. The kit also includes a binding molecule, such as hereinabove described, which binds to an oligosaccharide which is at least triantennary, but does not bind to oligosaccharides which are monoantennary or diantennary. The kit also includes a labeled antibody which recognizes an epitope of prostate specific antigen.

In another alternative, a sample suspected of containing prostate specific antigen is subjected to immunoprecipitation or to immunoaffinity purification using an antibody which recognizes prostate specific antigen. Isolated prostate specific antigen then is subjected to gel electrophoresis, such as, for example, sodium dodecyl sulfate-polyacrylamide gel electrophoresis, and transferred to an appropriate membrane, such as a polyvinylidene fluoride (PVDF) membrane. Appropriate bands then are excised from the membrane, and treated with an exoglycosidase or with a combination of an exoglycosidase and a neuraminidase to release the oligosaccharides from the prostate specific antigen. The oligosaccharides then are labeled and then analyzed through separation of the oligosaccharides on a gel. The gel then is analyzed for the presence of oligosaccharides which are at least triantennary.

Although the present invention has been described with respect to the diagnosis of cancer of the prostate through the detection of prostate specific antigen having linked oligosaccarides which are at least triantennary, the method of the present invention may be employed to detect antigens having linked oligosaccharides which are at least triantennary, and which are associated with cancer other than cancer of the prostate, such as, for example, breast and colon cancer. Such antigens may be detected by methods such as those hereinabove described with respect to the detection of the prostate specific antigen having linked oligosaccharides which are at least triantennary.

Figure 1:
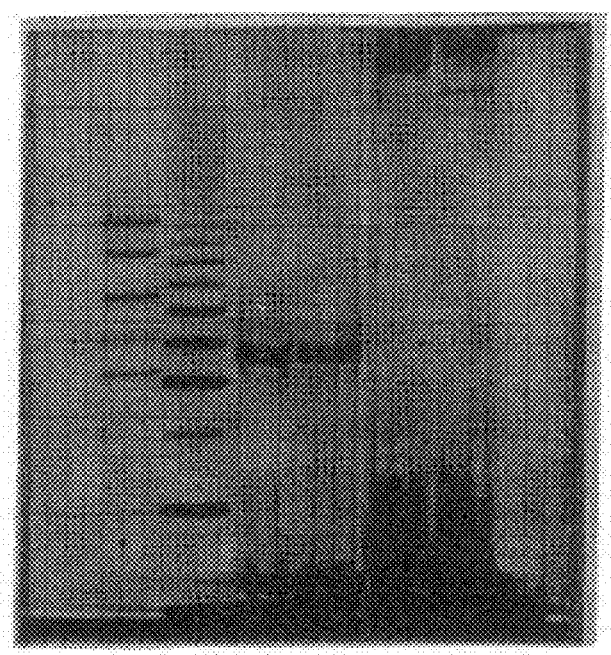
FIG. 1 shows the results obtained by releasing oligosaccharides from PVDF bound prostate specific antigen by PNGaseF, labeling the oligosaccharidase with ANTS, and separating the oligosaccharides by oligosaccharide PAGE. Oligosaccharide markers are shown in Lane 1. Lane 2 is an ANTS-labeled dextran standard (Glyko). Lanes 3 and 4 show oligonucleotides released from normal PSA. Lanes 5 and 6 depict oligosaccharides released from transformed PSA (i.e., PSA from prostate cancer cells.).
Figure 2:
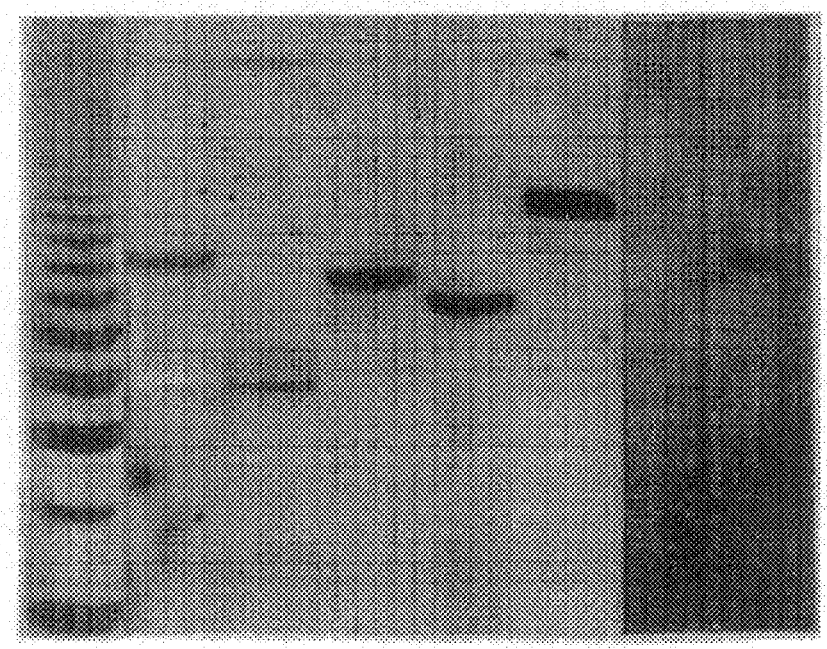
FIG. 2 shows the results of PAGE analysis of oligosaccharides from normal PSA and PSA having oligosaccharides that are at least triantennary. oligosaccharides were released from PVDF membrane bound PSA by PNGaseF and then treated with Neuraminidase 3. ANTS labeled samples were separated by oligosaccharide PAGE. Lane 1 is a dextran standard (Glyko). Lanes 2 and 8 are oligosaccharides from normal PSA treated with Neuraminidase 3. Lane 3 is an oligosaccharide from normal PSA. Lane 4 is an asialobiantennary oligosaccharide from PSA wherein fucose was not removed from the core chitobiose moiety of PSA. Lane 5 is an asialobiantennary oligosaccharide from PSA wherein fucose was removed from the core chitobiose moiety with fucase (Glyko). Lane 6 is an asialotriantennary oligosaccharide marker. Lane 7 is an oligosaccharide released from transformed PSA treated with Neuraminidase 3.

The invention now will be described with respect to the following example; however, the scope of the present invention is not intended to be limited thereby.

EXAMPLE 1

The LNCaP cell line (Young, et al., *Cancer Research*, Vol. 51, pgs. 3748–3752 (Jul. 15, 1991)) was grown in RPMI1640 containing 10% fetal calf serum and was stimulated with 50 to 100 nM androgen (5-β-androstan-17β-ol-3-one). Conditioned medium was collected one to two weeks after stimulation and the secreted PSA was estimated by the Hybritech Tandem-E PSA ELISA kit. Secreted PSA from the conditioned medium was purified by immunoprecipitation or by immunoaffinity purification using a polyclonal anti-human PSA antibody obtained commercially. Normal PSA or PSA purified from the LNCaP cell line was subjected to SDS-PAGE and was transferred overnight to a PVDF membrane. The membrane was stained with 0.1% Ponceau S, the appropriate bands were excised and then were treated either with the exoglycosidase peptide N-glycosidase F (PNGaseF), which cleaves Asn-linked oligosaccharide at β-aspartylglycosylamine of glycopeptides and glycoprotein, alone or with a combination of PNGaseF and Neuraminidase 3 (Glyko). The released oligosaccharides were labelled with the fluorophore 8-aminonaphthaline 1, 3, 6-trisulfonate (ANTS), also described in Stack, et al., *Glycobiology*, Vol. 2, No. 1, pgs. 85–92 (1992), and analyzed by fluorophore assisted carbohydrate electrophoresis, also known as FACE, which entails the analysis of fluorophore-labeled oligosaccharides by polyacrylamide gel electrophoresis, or PAGE. FACE is described further in Jackson, *Anal. Biochem*, Vol. 216, pgs. 243–252 (1994), and in Hu, *J. of Chrom.*, Vol. 705A, pgs. 89–109 (1995).

EXAMPLE 2

Antibodies to PSA are pre-bound to the surface of a 96 well microtiter plate. An aliquot of 100 µl of serum and 100 ul of diluent (PBS with 0.3% bovine serum albumin, pH 7.2, and sodium azide, 0.05%) is added to the wells. The microtiter plate then is incubated for one hour at 37° C. The solution then is discarded, and the wells are washed four times with 250 µl of diluent at room temperature. 200 µl of a solution of digoxigenin labeled lectin PHA-L at a concentration of 2 µg/ml is added to each well. The microtiter plate then is incubated for one hour at 37° C. The solution then is discarded, and each well is washed four times with 250 µl of diluent at room temperature. Each well then is contacted with a solution containing 150 mU/ml of peroxidase labeled antibody to dioxigenin. The plate then is incubated for one hour at 37° C. The solution then is discarded, and each well is washed four times with 250 µl of diluent at room temperature. 200 µl of peroxidase substrate (ABTS, Boehringer Mannheim) then is added to each well, and the plate is incubated for 30 to 60 minutes at room temperature. Absorbance using an ELISA reader at 405 nm with a reference wavelength at approximately 490 nm then is measured for each sample.

It is to be understood, however, that the scope of the present invention is not to be limited to the specific embodiments described above. The invention may be practiced other than as particularly described and still be within the scope of the accompanying claims.

What is claimed is:

1. A kit for detecting prostate specific antigen linked to an oligosaccharide which is at least triantennary, comprising:
   (a) an antibody which recognizes an epitope of prostate specific antigen;
   (b) a solid support which supports said antibody; and
   (c) a binding molecule which binds to oligosaccharides which are at least triantennary but does not bind oligosaccharides which are biantennary or monoantennary.

2. The kit of claim 1 wherein said binding molecule is PHA-L.

* * * * *